United States Patent [19]
Schmidt et al.

[11] Patent Number: 5,578,300
[45] Date of Patent: Nov. 26, 1996

[54] TREATMENT OF ALLERGIC CONTACT DERMATITIS

[75] Inventors: Richard J. Schmidt, Penarth; Lip Y. Chung, Cardiff, both of United Kingdom

[73] Assignee: University College Cardiff Consultants Limited, Cardiff, United Kingdom

[21] Appl. No.: 69,630

[22] Filed: Jun. 1, 1993

[30] Foreign Application Priority Data

Jun. 3, 1992 [GB] United Kingdom ............ 9211736

[51] Int. Cl.$^6$ .................. A61K 33/40; A61K 38/39; A61K 31/725; A61K 9/70
[52] U.S. Cl. ............ 424/78.08; 424/484; 424/486; 424/443; 514/862
[58] Field of Search .............. 424/78.05, 484, 424/486, 443, 445, 447, 448, 499; 514/944, 858–865

[56] References Cited

U.S. PATENT DOCUMENTS

| | | | |
|---|---|---|---|
| 4,009,282 | 2/1977 | Vorhees | 514/863 |
| 4,438,102 | 3/1984 | Ganci | 424/130 |
| 4,990,339 | 2/1991 | Scholl et al. | 424/443 |

FOREIGN PATENT DOCUMENTS 2076286  2/1981  United Kingdom.

9000899  2/1990  WIPO.

OTHER PUBLICATIONS

Picardo et al., Biosis (File 5) Accession No. 9402891 and British J. Dermatol., 126(5):450–455, Abstract (1992).

Burdon et al. (1990) in Stress Proteins, Induction and Function, "Active Oxygen Species and Heat Shock Protein Induction", pp. 19–25.

Santoro et al. (1990) in Stress Proteins. Induction and Function, "Induction of HSP70 by Prostaglandins", pp. 27–44.

Miya et al. (1980) International J. of Biological Macromolecules, "I.r. Spectroscopic Determination of CONH Content in Highly Deacylated Chitosan", 2:323–324.

Sannan et al. (1978) Polymer, "Studies on Chitin:7.I.r. Spectroscopic Determination of Degree of Deacetylation", 19:458–459.

Boveris (1977) Analytical Biochemistry, "Evaluation of Horseradish Peroxidase–Scopoletin Method for Measurement of Hydrogen Peroxide Formation in Biological Systems", 80:145–158.

Primary Examiner—Edward J. Webman
Attorney, Agent, or Firm—Kohn & Associates

[57] ABSTRACT

A method of treatment of allergic contact dermatitis, which comprises treating a patient with a formulation capable of inducing oxidative stress and a heat shock response so as to convert the allergic reaction of the allergic contact dermatitis to an irritant reaction.

2 Claims, No Drawings

5,578,300

TREATMENT OF ALLERGIC CONTACT DERMATITIS

FIELD OF THE INVENTION

The present invention is concerned with a method of treatment of allergic contact dermatitis.

BACKGROUND OF THE INVENTION

Mild heat shock may be induced in skin as a result of the skin temperature rising to about 45° C. and during conditions of oxidative stress and leads to induction of heat shock protein (or stress protein) formation. The heat shock response is regarded as a survival strategy which serves to protect living cells against temperature and other stresses. It is known that hydrogen peroxide is able to induce the heat shock response (Burdon R H, Gill V, & Rice Evans C. Active oxygen species and heat shock protein induction. In: Stress Proteins. Induction and function. pp. 19–25. Schlesinger M J, Santoro M G, & Garaci E (Eds). Springer-Verlag, Berlin, 1990) and also to generate oxidative stress. It is also known that prostaglandins can induce heat shock protein formation (Santoro M G, Garaci E, & Amici C. Induction of HSP70 by prostaglandins. In: Stress Proteins. Induction and function. pp. 27–44. Schlesinger M J, Santoro M G, & Garaci E (Eds). Springer-Verlag, Berlin, 1990).

Oxidative stress is a perturbation of redox homeostasis in favor of higher levels of oxidizing species relative to reducing species and is essentially a shift in the thiol/disulfide status of tissue biochemistry in favor of higher levels of disulfides.

Materials for inducing heat shock, such as hydrogen peroxide and polymeric materials capable of generating hydrogen peroxide, have previously been used for wound healing. In non-healing wounds, high levels of hydrogen peroxide (in the range of $10^{-6}M$ to about 1M) may serve to initiate the inflammatory phase of wound healing during which wound debris is removed. Low levels of hydrogen peroxide (around $10^{-8}M$ to $10^{-6}M$) are capable of stimulating fibroblast proliferation during later reconstructive stages of wound healing.

The allergic contact dermatitis reaction is however distinct from the wound healing reaction. Allergic contact dermatitis is regarded essentially as a response arising initially from the activity of antigen-presenting cells and subsequently from the activities of T cells when altered (or foreign) protein is detected by the immune system. Although this may lead to a visible inflammatory and eczematous or bullous reaction, soft tissue breakdown and ulcer formation to form a wound is an occasional but not an inevitable outcome. In contrast, a wound may be regarded as a lesion arising directly from soft tissue breakdown.

Allergic contact dermatitis can be either an acute or chronic eruption, and currently available therapy is varied according to the nature of the eruption.

Current methods of treatment of acute allergic contact dermatitis can involve any of the following: application of cool water, Burrow's solution (typically for 5 to 10 minutes every two to four hours), calamine lotion, topical application of fluorinated corticosteroids in a gel base, systemic corticosteroids (such as ACTH-gel, about 80 units being given intramuscularly followed by at least one further such injection), or a prescribed course of corticosteroid tablets such as dexamethasone.

Chronic allergic contact dermatitis is generally treated by application of topical corticosteroids, such as triamcinolone acetonide followed by less potent corticosteroids such as hydrocortisone or desonide. Chronic hand eczema can also be treated by Grenz ray.

The above do not however provide satisfactory therapeutic treatment of allergic contact dermatitis, and it is an object of the present invention to provide an improved method and formulation for the treatment of allergic contact dermatitis.

SUMMARY OF THE INVENTION

There is provided by the present invention a method of treatment of allergic contact dermatitis, which method comprises treating a patient, typically by application to the skin, with a formulation capable of inducing oxidative stress and the heat shock response, so as to convert the allergic reaction of the allergic contact dermatitis to an irritant reaction.

It is thought that the oxidative stress induces the heat shock response and converts the allergic reaction of the dermatitis to an irritant reaction, the latter having a shorter time span than the former. It is further thought that the heat shock inhibits the enzyme NADPH oxidase.

There is further provided by the present invention a formulation capable of inducing oxidative stress and heat shock response, the formulation being in a form suitable for treatment of allergic contact dermatitis.

The present invention has particular applicability in the treatment of allergic dermatitis induced by poison ivy or the like, and therefore provides a remedy for a prevalent skin complaint experienced by many sufferers throughout the U.S.A.

DETAILED DESCRIPTION OF THE INVENTION

The formulation according to the invention preferably comprises a hydrogen peroxide source; preferably the latter comprises a hydrogen peroxide precursor, although it is envisaged that the source may initially comprise hydrogen peroxide per se. It is further preferred that the hydrogen peroxide is generated by, and/or released from, the formulation at a level of about 1.0 to $100 \times 10^{-7}M$ over a 24 hour period as measured by a horseradish peroxidase-scopoletin assay (as described below) using a sample concentration of 0.05 to 0.50% w/v, so as to be capable of permeating the skin in sufficient quantity to enhance the level of oxidative stress and induce the heat shock response.

It is preferred that the hydrogen peroxide precursor comprises a polymeric material capable of generating hydrogen peroxide. Preferred polymeric materials include chitin, chitosan, gelatin, pectin, and derivatives of these materials, or a material such as that commercially available under the trade mark Granuflex (a material comprising hydrocolloid granules comprising gelatin, sodium carboxymethylcellulose and pectin). The hydrogen peroxide generating capacity of the latter material has been ascribed to the gelatin and pectin. The polymeric material may therefore typically comprise a composition comprising gelatin and pectin.

A formulation for use according to the present invention is typically a hydrogel or hydrocolloid. The hydrogel or hydrocolloid may be in the form of a paste or sheet, suitable for topical application typically under a semi-occlusive tape such as that commercially available under the trade mark Pharmaclusive. Alternatively, the formulation may be impregnated in a protective covering such as a film, foam, or pad.

The method preferably involves application of the formulation to a patient's skin. The method may further advantageously involve heat treatment at 45° to 50° C.

The formulation may further comprise prostaglandins which further contribute to the induction of the heat shock response.

The following Examples 1 to 4 illustrate assay of hydrogen peroxide-generating activity of various materials.

EXAMPLE 1

A hydrogen peroxide assay was carried out as follows.

Reagents

Catalase (from bovine liver, ammonium sulphate and thymol free), scopoletin, horseradish peroxidase (type I), and other chemicals of high purity were obtained from Sigma Co. Ltd., Poole, Dorset, U.K. The chitin/chitosan samples were supplied by Protan Biopolymers, Drammen, Norway. The degree of deacetylation (a measure of chitosan content) of these materials was estimated using infra-red spectroscopy as previously described by Miya M, Iwamoto R, Yoshikawa S, and Mima S (I.R. spectroscopic determination of CONH content in highly deacylated chitosan; International Journal of Biological Macromolecules, 1980, volume 2, pp. 323–324) and by Sannan T, Kurita K. Ogura K, and Iwakura Y. (Studies on chitin: 7. I.R. spectroscopic determination of degree of deacetylation; Polymer, 1978, volume 19, 458–459). Other polysaccharides and polysaccharide-based materials were commercial products obtained from various suppliers.

A procedure adapted from that previously described by Boveris A, Martino E, & Stoppani AOM (Evaluation of the horseradish peroxidase-scopoletin method for the measurement of hydrogen peroxide formation in biological systems. Analytical Biochemistry, 1977, volume 80, pp. 145–158) was used.

The reaction mixture contained, in a final volume of 6 milliliters, $5\times10^{-7}$ moles/liter scopoletin, test material (0.05–0.50% w/v) and 50 millimoles/liter potassium dihydrogen orthophosphate/potassium hydroxide buffer pH 7.4.

The reaction was started by adding 60 microliters of horseradish peroxidase (HRP, 80 units/milliliter). The mixture was agitated and kept in the dark at 37° C. The change in fluorescence of the mixture was monitored at time intervals (excitation: 320 nm; emission: 460 nm).

The catalase control consisted of $5\times10^{-7}$ moles/liter scopoletin, test material (0.05–0.50% w/v), 400 units/milliliter catalase, 0.8 units/milliliter HRP and 50 millimoles/liter potassium dihydrogen orthophosphate/potassium hydroxide buffer pH 7.4 in a final volume of 6 milliliters. The scopoletin control consisted of $5\times10^{-7}$ moles/liter scopoletin, test material (0.05–0.50% w/v) and 50 millimoles/liter potassium dihydrogen orthophosphate/potassium hydroxide buffer pH 7.4.

The level of hydrogen peroxide formed is related to the difference in the fluorescence of the reaction mixtures of the test materials with and without catalase. The level of hydrogen generated by the test materials expressed in moles/liter was derived from a standard curve constructed with known concentrations of standard hydrogen peroxide ($10^{-6}$–$10^{-8}$ moles/liter). A known amount of standard hydrogen peroxide was added to the reaction mixture containing the test material, scopoletin and HRP to obtain a correction factor for the test materials inhibitory effect on the assay. Thus, the level of hydrogen peroxide detected without and with correction for the inhibitory effect is termed the "lower limit" and the "upper limit" respectively. The actual levels of hydrogen peroxide released by the samples lie between the upper and lower limits.

EXAMPLE 2

Protein chitin/chitosan samples (0.05–0.50% w/v) were assayed using the technique described in Example 1.

Hydrogen peroxide was generated by the samples. The level of hydrogen peroxide generated was related to the concentration and degree of deacetylation as shown in Table 1.

EXAMPLE 3

The following polysaccharides were investigated for their hydrogen peroxide generating capacity—chitosan lactate (Protan), chitin (Sigma), pectin (SquibbDerm), gelatin (Courtaulds), sodium carboxymethylcellulose (SquibbDerm) and Ca/Na alginate (Courtaulds).

The results are shown in Table 2.

EXAMPLE 4

A selection of polysaccharide-based wound dressings, as shown in Table 3, were also investigated for their hydrogen peroxide generating capacity. As can be seen in Table 3, the material commercially available under the trade mark Granuflex Granules, was the only test dressing which generated hydrogen peroxide.

The following Example illustrates the present invention.

EXAMPLE 5

Two 10 microliter applications of a known skin allergen helenin (0.15 % w/v) in ethanol were made to the left forearm of an individual previously sensitized to this allergen.

A further 10 microliter application of helenin was made to the right forearm and was left untreated as a control. The applications were left uncovered and untreated for 16 hours. During this time, a pruritic skin reaction (1+) began to evolve.

Treatment of the reactions on the left forearm was then initiated. To one reaction site was applied a hydrogen peroxide generating hydrocolloid paste containing gelatin and pectin. To the second was applied a square of poly(ethylene oxide) hydrogel which does not generate hydrogen peroxide. The whole area was covered with a semi-occlusive adhesive tape. After 12 hours, the treatments were removed.

Both reactions had evolved into slightly oedematous erythematous papulovesicular eruptions (2+) of 2 centimeter diameter. Pruritus was perceptible but not uncomfortable. The reaction treated with the hydrogen peroxide generating hydrocolloid paste was clearly more intense than that treated with the hydrogel sheet; both were more intense than the control reaction on the right forearm. The whole area of the left forearm was then placed under hot running water at 50° C. for 1 minute, dried, and the treatments renewed by exchanging the hydrocolloid mixture and hydrogel applications, i.e., a cross-over protocol.

After a further 12 hours, the treatments were removed and the area examined. The hydrocolloid-treated reaction again appeared noticeably more erythematous than the hydrogel treated reaction. The overall intensity (2+) of the reactions was otherwise unchanged. As before, the whole area was then placed under hot running water for 1 minute, dried, and both reactions being covered with the hydrogel.

After a further 12 hours the treatments were again removed, heat treated for 1 minute, and covered with hydrogel for another 12 hours prior to final heat treatment.

After a total of about 72 hours all swelling and itching had subsided from the hydrocolloid treated forearm, and reactions had essentially resolved with only slight reddening still evident on the sites of helenin application. In addition, there was little evidence of post-inflammatory hyperpigmentation (when observed at 7 days). In contrast, the untreated skin reaction on the right arm took about 3 weeks to resolve, was at times almost intolerably pruritic, and resulted in distinct post-inflammatory hyperpigmentation.

What we claim is:

1. A method of treatment of allergic contact dermatitis which comprises treating the skin of a patient with a hydrogen peroxide generating polymeric material comprising gelatin and pectin so as to induce an oxidative stress and a heat shock response in the skin of the patient whereby the allergic reaction of the allergic contact dermatitis is converted to an irritant reaction.

2. A method according to claim 1, wherein said polymeric material comprises hydrocolloid granules comprising gelatin, sodium carboxymethylcellulose and pectin.

* * * * *